(12) United States Patent
Foser et al.

(10) Patent No.: US 7,648,362 B2
(45) Date of Patent: Jan. 19, 2010

(54) DENTAL RESTORATION AND A METHOD FOR PRODUCING A DENTAL RESTORATION

(75) Inventors: Hans-Peter Foser, Balzers (LI); Urs Spirig, Balzers (LI)

(73) Assignee: Ivoclar - Vivedent AG, Schaan (LI)

( * ) Notice: Subject to any disclaimer, the term of this patent is extended or adjusted under 35 U.S.C. 154(b) by 80 days.

(21) Appl. No.: 10/782,451

(22) Filed: Feb. 19, 2004

(65) Prior Publication Data

US 2005/0084823 A1    Apr. 21, 2005

(30) Foreign Application Priority Data

Oct. 17, 2003    (DE)    ................. 103 48 369

(51) Int. Cl.
*A61C 13/08*    (2006.01)
(52) U.S. Cl. .................... 433/204; 433/169; 433/202.1; 433/212.1; 433/218
(58) Field of Classification Search ............. 433/202.1, 433/204, 212.1, 218, 169; 264/16–19
See application file for complete search history.

(56) References Cited

U.S. PATENT DOCUMENTS

| | | | |
|---|---|---|---|
| 4,398,887 A | | 8/1983 | Balde |
| 4,585,417 A | * | 4/1986 | Sozio et al. .............. 433/202.1 |
| 4,764,118 A | | 8/1988 | Touati |
| 4,828,117 A | | 5/1989 | Panzera |
| 5,314,335 A | * | 5/1994 | Fung .......................... 433/223 |
| 5,346,397 A | * | 9/1994 | Braiman ..................... 433/223 |
| 6,010,337 A | * | 1/2000 | Billet et al. ................. 433/218 |
| 6,183,256 B1 | * | 2/2001 | Fisher et al. ................ 433/219 |
| 6,250,926 B1 | | 6/2001 | Foser et al. |

FOREIGN PATENT DOCUMENTS

| | | |
|---|---|---|
| DE | 2102564 A1 | 4/1972 |
| DE | 88 01 654.4 U1 | 6/1988 |
| DE | 41 33 690 A1 | 4/1993 |
| DE | 4133690 A1 | 4/1993 |
| DE | 43 05 169 A1 | 8/1994 |
| DE | 196 28 930 C1 | 10/1997 |
| DE | 198 50 451 C1 | 3/2000 |
| FR | 2 577 796 A1 | 8/1986 |
| JP | 2000-139957 | 5/2000 |
| JP | 2002-153492 | 5/2002 |
| WO | WO 98/03128 A1 | 1/1998 |

* cited by examiner

*Primary Examiner*—Cris L Rodriguez
*Assistant Examiner*—Michael R Ballinger
(74) *Attorney, Agent, or Firm*—Alan S. Korman; John C. Thompson

(57) ABSTRACT

A dental restoration is provided which includes a base structure and a pre-fabricated over structure which at least partially covers the base structure. An interconnecting material interconnects hardened bite elements of the over structure with the base structure. In accordance with the method of producing a dental restoration, the interconnecting material applied onto the base structure is hardened fully after the over structure has first been applied onto the still malleable interconnecting material.

16 Claims, 3 Drawing Sheets

DENTAL RESTORATION AND A METHOD FOR PRODUCING A DENTAL RESTORATION

CROSS-REFERENCE TO RELATED APPLICATIONS

This application claims foreign priority benefits under 35 U.S.C. §119 from German patent application Ser. No. 103 48 369.1 filed Oct. 17, 2003.

TECHNICAL FIELD

The present invention relates to a dental restoration and a method for producing the dental restoration.

BACKGROUND OF THE INVENTION

A known dental restoration is disclosed in DE 41 33 690. In connection with this known dental restoration, plastic finished partial crowns and bite surfaces are used, which are applied as an integral entirety onto the base structure. After the application of these components onto the base structure, the plastic semi-finished component is hardened via irradiation with ultraviolet, or UV, light, so that a corrected bite surface is thus made available. Such bite surfaces are comparatively soft. At the same time, intensive hand finishing work of such bite surfaces is required to configure the bite surfaces into configurations which simulate the dental structures which are to be restored and the dental restoration which is produced by this approach is heavily dependent upon the capability of the dentist or, as the occasion may be, upon the capability of the dental technician, to produce the desired tooth protuberance shape.

Moreover, finished elements for the production of dental restorations are already known as is disclosed, for example, in U.S. Pat. No. 6,250,926. The approach disclosed in this publication is suitable for the creation of a dental restoration which is configured by covering a metal frame with an opaque covering and thereafter applying thereon a layer of dentin material ceramic. The dental restoration precisely establishes the shape of the incisal surfaces. The ceramic layer, or coating, which is configured in approximation of the dentin, must have an exact shape so that no orientation errors can arise. Via the application of two layers or coatings, an aesthetic corresponding result can be achieved; however, a decidedly precise handling of the piece is required in order to assuredly prevent the creation of dental positioning errors.

OBJECTS AND SUMMARY OF THE INVENTION

The present invention offers a solution to the challenge of providing a dental restoration, as well as a method of producing a dental restoration, which permits a flexible delivery of dental service via rapid production of the dental restoration without posing special hand finishing requirements.

The present invention includes a dental restoration having a bite surface of predetermined configuration, which can be produced as a pre-fabricated over structure and which can, therefore, be made available with good quality in a cost-favorable manner.

The present invention permits one to ensure, in a simple manner, a precise adjustment of the teeth in the occlusion position in that, for example, an orientation can be undertaken in a conventional manner in an articulator. The inner contour of the pre-fabricated over structure is, in this connection, substantially concavely configured and the outer contour of the base is, in a corresponding manner, convexly configured. Even if the relevant contours clearly deviate from, for example, the typical half-spherical and uniform over surface shape of a tooth stump prepared in a conventional manner, there is still a good possibility for precise adjustment at least for the reason that the inventive interconnecting material of this invention covers the gap between the inner contour of the over structure and the outer contour of the base structure.

If the coating of the interconnecting material amounts to, for example, 0.8 mm or 1 mm, an adjustment of, for example, about 0.5 mm is not a problem, whereby it is preferred that the over structure is, initially, comparatively loosely pressed into position and the precise adjustment is then effected via further "follow up pressing in" of the over structure, with corresponding orientation efforts, onto the bite surfaces.

In accordance with the present invention, it is also advantageous that one uses the respective antagonistic tooth as the pressure-applying element in the articulator, as, in this manner, an optimization of the dental restoration positioning automatically ensues.

It is to be understood that also, for example, the Benett angle can be taken into account, and it is also possible, without further effort, to provide coverage for the range of teeth shapes typically arising in a conventional dental practice with a predetermined count or number of prepared bite surface elements.

In accordance with the present invention, it is particularly advantageous, moreover, that the interconnecting material, which is preferably comprised of a hardenable plastic which can be hardened in-situ, develops a certain dampening effect so that the wear of the antagonistic teeth is also reduced even in the event that ceramic is deployed for the over structure.

In accordance with the present invention, it is further particularly advantageous if a base structure covers at least one tooth stump in a unitary manner. It is also possible to so configure the base structure—including via, as the occasion arises, the deployment of an additional frame—such that several tooth stumps are simultaneously covered, whereby a unitary configuration can be realized.

In accordance with the present invention, the interconnecting material can be allowed to harden in place in a surprisingly simple manner. It is possible to undertake a thermal hardening for the regions of the interconnecting material, which are covered by the base structure. In this connection, a self-hardening plastic material is considered.

Free lying regions of the interconnecting material that is, side regions of the respective tooth also permit the configuration of a light-hardenable plastic material. Such side regions and, as well, regions of the tooth comprised of aesthetically less relevant bite surfaces themselves, can be covered by the base structure in a comprehensive manner with an opaque-appearing material so that the inventive approach offers an aesthetically satisfactory translucent appearance.

Surprisingly, despite the use of several different materials, such as the interconnecting material and, as the occasion arises, different light-polymerizable plastic materials for the side region, and despite the different heat expansion coefficients, no edge gaps or cracks are created. By virtue of the coating of, initially, a first interconnecting material for the securement of the base structure on this interconnecting material, the coating of a second interconnecting material for the securement of the over structure on the base structure, and, ultimately, the securement of the over structure itself, respectively comparatively thin coatings are formed which exhibit correspondingly reduced material contraction properties. A time-consuming firing of the assembly can be omitted which favorably benefits a reduction of the cycle time in the dental laboratory.

A dental restoration produced in accordance with the present invention permits, as well, the polishing thereof in a good manner, whereby the material choice for the over structure is not limited to ceramic material but can, as well, comprise plastic, including plastic in a prefabricated form.

In accordance with the present invention, it is additionally particularly advantageous if the bite element extends over the entire mastication surface in a crack-free manner. In this manner, a stable restoration as well as a solid surface in the most strongly stressed regions of the restoration is ensured.

In accordance with the present invention, it is further advantageous that, via the somewhat elastic coating of the additional interconnecting material, fatigue breaks in the over structure occur in a significantly less frequent manner, as the pressure peaks, which typically manifest themselves in the tooth protuberance flanks during mastication, are better captured and compensated by the inventive approach.

In accordance with the present invention, either comparatively hard plastic or desired ceramic materials can be used for the over structure. Thus, an aluminum oxide ceramic, a zirconium oxide ceramic, or a mixture of these ceramics can be deployed or other oxide ceramics can be deployed without further effort.

In connection with the production of a dental restoration in accordance with the present invention, the production preferably entails a predetermined excess or spillover of the interconnecting material. Initially, the required preparation is undertaken for the production of an inventive dental restoration. The base structure is formed into a finished condition such as, for example, with a metal coating or formed of complete ceramic or formed in another suitable desired manner. A model is molded of gypsum in a conventional manner. An interconnecting material is applied onto the base structure and, in fact, has a viscosity which still permits deformation while, however, not permitting deformation of the interconnecting material due solely to the force of gravity.

The over structure is configured with an inner contour which is larger than the outer contour of the base structure but which is, however, compatibly configured therewith. The deposition of a remainder coating of interconnecting material permits application of the over structure onto the base structure and the assembled structure is preferably adjusted in the articulator. The over structure is pressed into the interconnecting material and a precise adjustment is undertaken in the desired manner. A hardening out of the interconnecting material is effected in this position. This can be effected via a self-hardening plastic material which hardens organically or, however, can also be effected by other means such as, for example, via heat polymerizable plastic material having heat applied thereto. The spillover, which occurs laterally of the plastic, is removed preferably before the hardening out. It is also possible to remove a portion of the spillover before the hardening out and to remove the remainder of the spillover after the hardening out.

The inventive solution provides an improved restoration quality in view of the bite situation despite reduced production costs and despite a shortened improved cycle time.

DETAILED DESCRIPTION

Figure 1:
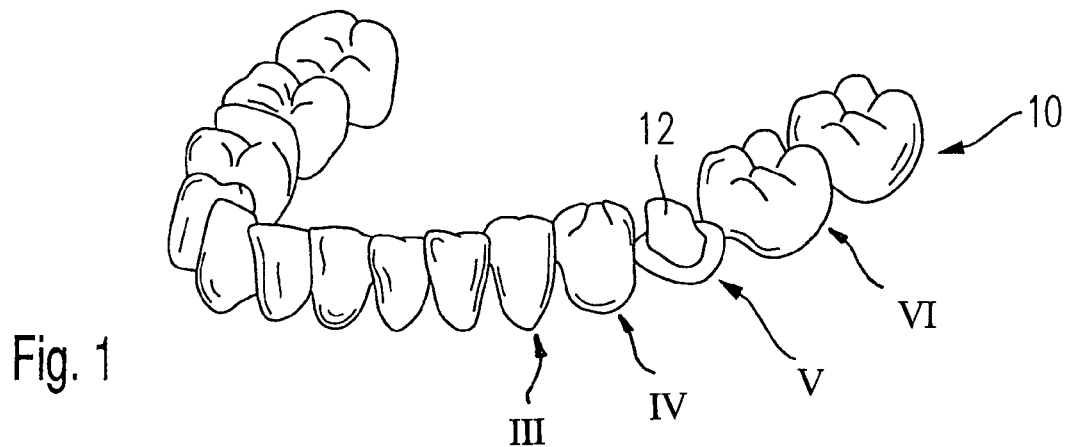
FIG. 1 is a perspective view of teeth and showing a pre-prepared tooth stump adapted to receive one embodiment of the dental restoration of the present invention.

FIG. 1 shows, in a schematic manner, the teeth of a lower jaw, the teeth being indicated generally at 10. In this illustration a pre-molar V has been prepared such that a tooth stump 12 is available.

Figure 2:
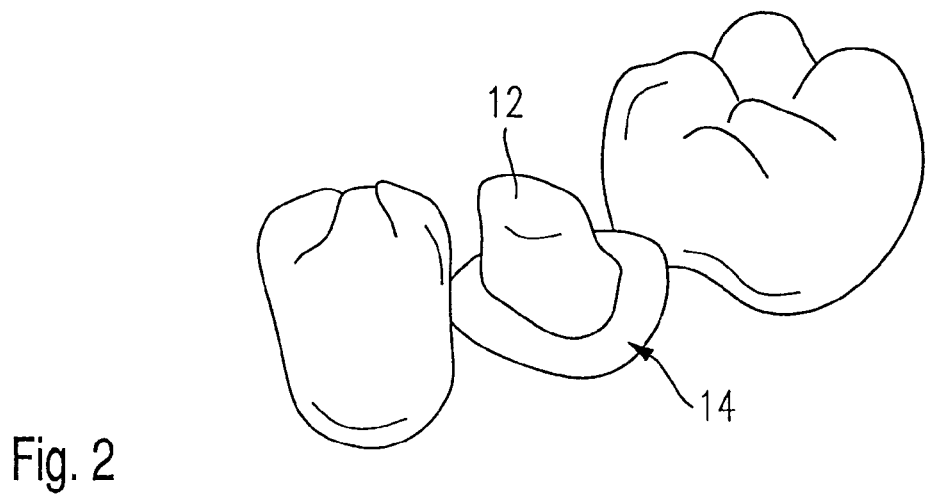
FIG. 2 is an enlarged perspective view of a portion of FIG. 1.

The tooth stump 12 comprises, in a conventional manner, a conventional stump configuration, which can be seen as well in FIG. 2 in an enlarged view thereof, whereby preparation borders 14 are created in the form of a socket extending in an annularly shaped manner about the tooth stump.

Figure 3:
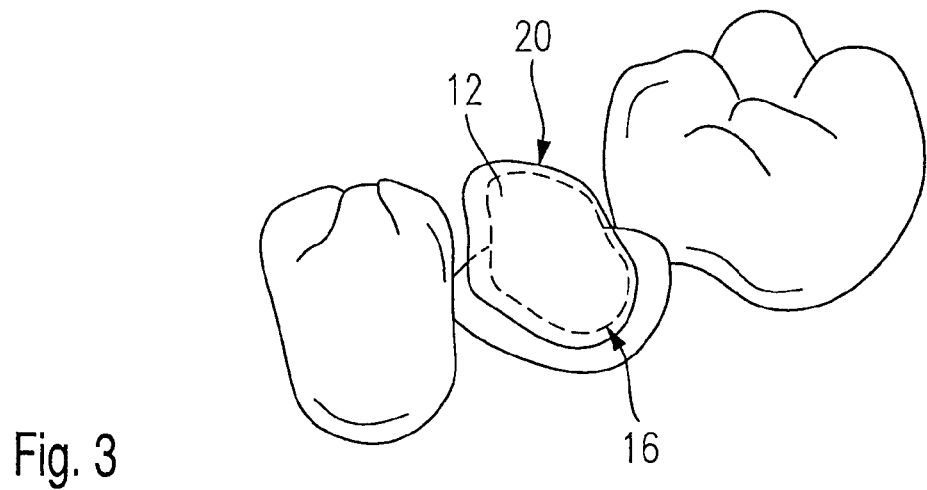
FIG. 3 is a perspective view of the portion of the one embodiment of the dental restoration shown in FIG. 2 showing, however, a base structure applied onto the tooth stump.

In accordance with the present invention, a custom dental restoration is to be applied onto the tooth stump 12. In this connection, as shown FIG. 3, a base structure 16 is initially applied onto the tooth stump. The base structure 16 is formed of a metal frame, which has been covered with a not-illustrated opaque-appearing material. The securement thereof follows with a conventional interconnecting material. The base structure 16 has a substantially uniform coating thickness.

The base structure 16 comprises an outer contour 20 which substantially corresponds to the outer contour of the tooth stump 12 but which, however, is somewhat rounder and larger. The tooth stump 12 is shown in broken lines in FIG. 3.

Figure 4:
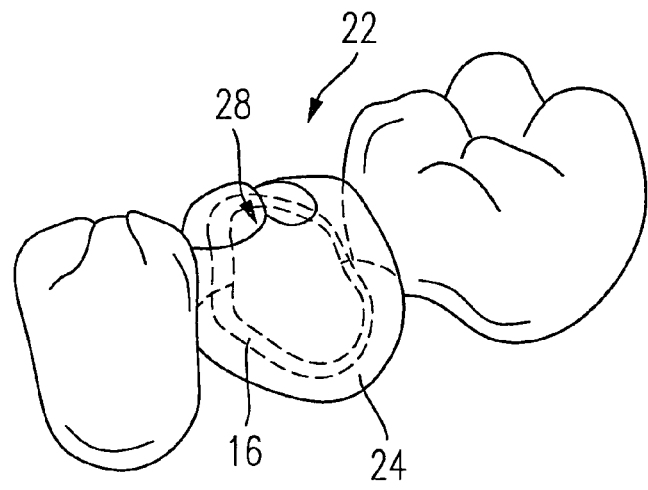
FIG. 4 is a perspective view of the dental restoration shown in FIG. 3 showing, however, a pre-fabricated over structure applied thereunto.

FIG. 4 shows one embodiment of the dental restoration 22 after the pre-fabricated over structure 24 has been applied onto the base structure 16. In FIG. 4, the base structure 16 is shown in broken lines and it can be seen that the base structure 16 is completely covered by the over structure 24 in this embodiment. The base structure terminates at the preparation borders 14 (compare FIG. 2) and, between the base structure and the over structure, an interconnecting material 26 has been applied (not illustrated in FIG. 4) which fills the entire layer-defining space between the inner contour of the over structure 24 and the outer contour of the base structure 16.

In order to prevent included or entrapped air, it is provided that the contact between the interconnecting material 26 and the inner contour of the over structure 24 initially occurs at the highest location 28. At this location, the thickness of the layer of the deformable interconnecting material is correspondingly relatively great and the shape of interconnecting material is accommodated to the shape of the over structure during the pressing down of the over structure, preferably in the articulator.

It is to be understood that the exact configuration can be accommodated to a wide range of requirements. Thus, it is also possible to provide a bite element for covering the bite surface and, thereafter, to provide side elements, which may be, as well, pre-prepared components, and which are applied by the pressing thereof into the interconnecting material. This configuration has the advantage that a slight angle accommodation of the bite surface is still possible, whereby it is to be understood that, initially, the angle accommodation should be effected and, thereafter, the side elements can be aligned with the top surface that is, positioned flush with the bite surface element.

Figure 5:
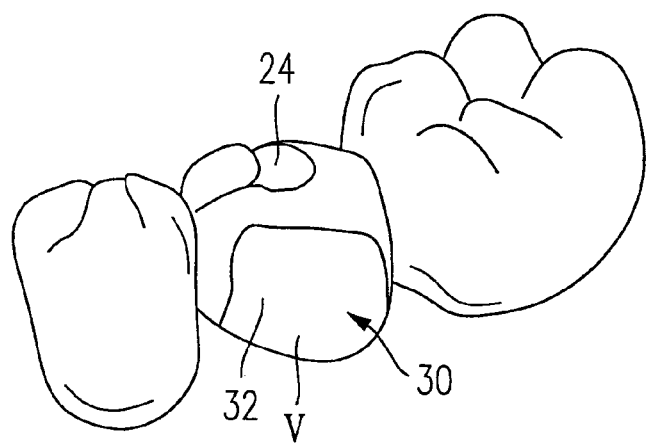
FIG. 5 is a perspective view of another embodiment of the inventive dental restoration having a modified over structure.

FIG. 5 shows another embodiment of the dental restoration of the present invention wherein the side surfaces 30 of the tooth V are not covered by the ceramic over structure 24. In this embodiment, a plastic material, preferably, a light-hardenable material 32, is provided on the side surfaces 30, this material being hardened after the installation of the over structure and after the conclusion of the top surface preparation that is, the making ready of a flush top surface.

The deployed interconnecting material between the base structure and the over structure can either be thermally hardenable plastic material, a self-hardening plastic material, or, for example, a dental or tooth cement as well. It is to be understood that the plastic material 32 can, as required, be configured in the same manner that is, for example, such material can also be a thermally hardenable plastic material whose top surface is relatively wear resistant.

Figure 6:
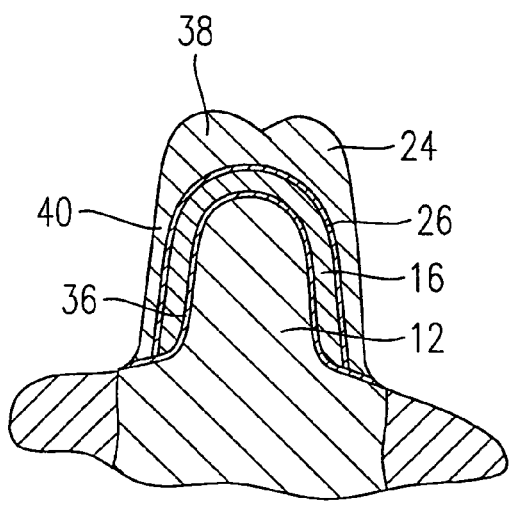
FIG. 6 is a side elevation sectional view of a representative inventive dental restoration.

FIG. 6 shows a representative dental restoration of the present invention in cross section. The reference numerals in FIG. 6 indicate identical elements as are described with respect to like-numbered elements shown in the other figures of the drawings. It is schematically indicated that a further interconnecting material 36 is provided between the tooth stump 12 and the base structure 16.

The over structure 24, in the illustrated embodiment, takes the form of the upper region formed by the bite element 38 as well as a covering element 40 which, in the manner of an apron, extends downwardly. Preferably, this extension of the over structure extends into mesial and distal regions of the tooth, whereat access thereto is significantly limited.

In accordance with the present invention, it is preferable that the dental restoration is, after its finishing that is, after obtaining a perfect or exact orientation between the base structure 16 and the over structure 24—accommodated to the teeth structure and, in this connection, that the second interconnecting material 36 is deployed in a conventional manner.

In a modification of the dental restoration of the present invention, it is provided, in lieu of the base structure, to deploy a special securement material which forms the base structure 16 and onto which the over structure 24 can be directly applied. This approach is especially suitable for small restoration requirements and permits the preparatory removal of the dentin to be limited to the minimum required mass.

Figure 7:
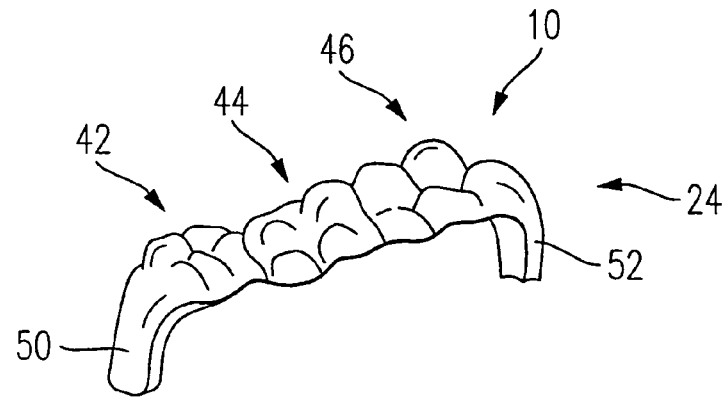
FIG. 7 is a perspective view of a further embodiment of the inventive dental restoration and showing the over structure thereof for a tooth restoration.

FIGS. 7 to 10 show embodiments of the inventive dental restoration which are suitable for the restoration of a plurality of teeth 10. As can be seen in FIG. 7, a multiple member pre-fabricated over structure 24 of a further embodiment of the dental restoration is illustrated. The over structure 24 comprises three bite elements 42, 44, and 46 corresponding respectively to the teeth IV, V, and VI and are, to this extent, multiple member configuration. An apron 50 extends downwardly on the mesial side of the bite element to communicate with the preparation border that is, along the side flanks of the tooth IV, which is turned toward the tooth III.

An apron 52 extends along the distal side surface of the tooth VI.

In the illustrated embodiment, the bite elements 42, 44, and 46 are configured adjacent one another as a unitary component, and the aprons 50 and 52 are likewise configured as a unitary component. It is to be understood, that in lieu of this configuration, a multiple component configuration of the bite elements 42-46 is also possible.

Figure 8:
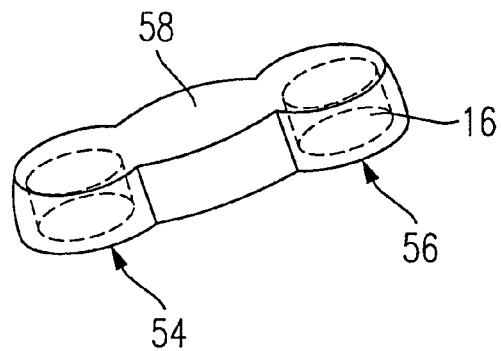
FIG. 8 is a perspective view of the base structure of the further embodiment of the dental restoration shown in FIG. 7.

A correspondingly configured base structure 16, which is suitable for receipt thereon of the over structure 24 in the embodiment shown in FIG. 7, is illustrated in FIG. 8. This base structure 16 comprises two bowl-shaped recesses 54 and 56 which are downwardly open and can receive correspondingly prepared tooth stumps; in the illustrated embodiment, for example, the tooth stumps of teeth IV and VI. A bridge region 58 is configured between these end regions, the bridge region supporting the bite element 44.

Also, in this embodiment, the outer contour of the base structure 16 is compatibly configured with the inner contour of the over structure 24.

Figure 9:
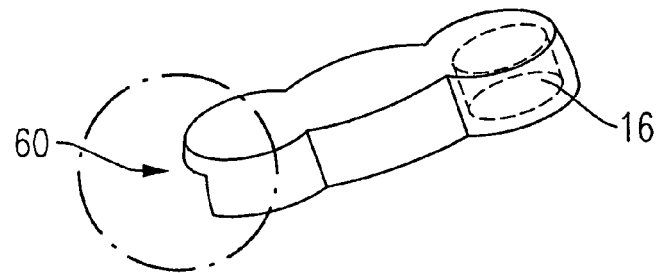
FIG. 9 is a perspective view of an additional embodiment of the dental restoration of the present invention and showing the base structure thereof in lieu of the base structure of the further embodiment of the dental restoration shown in FIG. 8.

FIG. 9 illustrates an additional embodiment of the dental restoration of the present invention, showing the base structure 16 thereof. In lieu of the recess 54, an attachment recess 60 is provided, which is suitable for the receipt therein of an attachment element (not illustrated).

Figure 10:
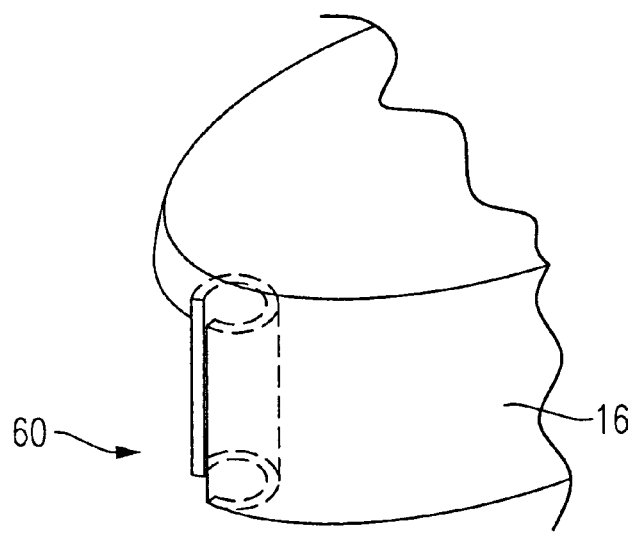
FIG. 10 is an enlarged perspective view of the additional embodiment of the dental restoration shown in FIG. 9.

FIG. 10 shows an enlarged illustration thereof. The attachment recess 60, which replaces the recess 54 of the FIG. 8 embodiment, is configured in a conventional manner such that a vertical removal of the attachment element seated therein is possible while, at the same time, ensuring a secure seating of the attachment element received therein. These seating and removal characteristics can be imparted by, for example, providing a corresponding conicity along the vertical axis in the area of the attachment recess 60. In other words, the recess may be cylindrical or conical, and it should have an axis parallel to the axis of the recess 56.

Another suitable desired interconnecting element can be deployed in lieu of the interconnecting material for securing the over structure 24 on the base structure 16 such as, for example, a positive mechanical inter-engagement between the over structure and the base structure.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A dental restoration, consisting of:
   a base structure (16) formed of a selected one of a single member and multiple members, the base structure being adapted to be placed on a selected one of a tooth stump of a tooth of the dental patient, interconnecting material on the tooth stump, a peg supported by a jaw of the dental patient, and an attachment element operable to be secured to neighboring tooth structure adjacent to the location at which the dental restoration is to be mounted, the base structure having inner and outer contours;

a pre-fabricated comparatively hard over structure (24) in the form of a molar or premolar which, when assembled with the base structure (16), at least partially covers the base structure (16), the over structure (24) having an inner contour and at least one pre-configured bite element (38) having a predetermined bite surface on an outer contour; and a single layer of light polymerizable elastic interconnecting material (26) for coupling the base structure (16) and the over structure (24) with one another, the interconnecting material filling the entire layer defining space between the inner contour of the over structure and the outer contour of the base structure, the base structure and over structure.

2. A dental restoration according to claim 1, wherein the over structure (24) has a covering element (40) that is interconnected with the bite element (38) and extends in at least partial coverage over at least one of a lingual, buccal, mesial, and distal region of the base structure (16), the covering element (40) being interconnected to the base structure (16) via the interconnecting material (26).

3. A dental restoration according to claim 2, wherein the dental restoration extends substantially to preparation borders of such teeth and, preferably, the covering element (40) covers the medial and distal sides of such teeth.

4. A dental restoration according to claim 2, wherein each respective portion of the over structure (24) formed by the bite element (38) and the covering element (40) is comprised of at least one of ceramic and plastic.

5. A dental restoration according to claim 4, wherein the covering element is formed of a ceramic which is a pre-prepared ceramic and, preferably, is a selected one of an aluminum oxide ceramic, a zirconium oxide ceramic, a glass ceramic, and a mixture of such ceramics.

6. A dental restoration according to claim 2, wherein each of the bite element (38) and the covering element (40) is comprised of ceramic.

7. A dental restoration according to claim 2, wherein the over structure (24) is configured as a single member component and the bite element (38) and the covering element (40) are comprised of the same material.

8. A dental restoration according to claim 1, wherein the interconnecting material (26) extends in a surface covering manner between the base structure (16) and the over structure (24) and, preferably, the interconnecting material (26) fills the interspatial area between the base structure (16) and the over structure (24).

9. A dental restoration according to claim 1, wherein the over structure (24) has an inner contour chat is substantially compatibly configured with respect to an outer contour of the base structure (16) and, preferably, the inner contour of the over structure (24) and the outer contour of the base structure (16) have respective circular shapes.

10. A dental restoration according to claim 1, wherein the bite element (38) extends over the entire mastication area of the dental restoration and the bite element (38) is, preferably, configured as a single member component.

11. A dental restoration according to claim 1, wherein the base structure (16) is a selected one of a metal frame, a metal ceramic frame, a ceramic frame, a plastic frame, and a plastic fiberglass frame.

12. A dental restoration according to claim 1, wherein the bite element (38) of the over structure (24) forms a protuberance that simulates a tooth protuberance of the tooth which the dental restoration is intended to simulate.

13. A method for producing a dental restoration, consisting of the steps of:

providing a base structure (16) which is formed of a selected one of a single member and multiple members, the base structure having inner and outer contours and being adapted to be on a selected one of a tooth stump of a tooth of the dental patient, interconnecting material on the tooth stump, a peg supported by a jaw of the dental patient, and an attachment element operable to be secured to neighboring tooth structure adjacent to the location at which the dental restoration is to be mounted;

providing an elastic single layer interconnecting material (26) which is a light polymerizable material, which interconnecting material is provided on the base structure;

disposing onto the interconnecting material (26), a pre-fabricated comparatively hard over structure (24) in a manner in which the over structure (24) at least partially covers the base structure (16), the over structure (24) having an inner contour and at least one pre-configured bite element (38) having a predetermined bite surface on an outer contour, the interconnecting material filling the entire layer-defining space between the inner contour of the over structure and the outer contour of the base structure; and after disposing the over structure (24) onto the interconnecting material (26), completely activating the interconnecting material (26) into its completely activated condition in which it securely interconnects the base structure (16) and the over structure (24) to one another, wherein the interconnecting material (26) is completely activated via irradiating with light to harden the interconnecting material (26).

14. A method for producing a dental restoration according to claim 13, wherein the step of disposing the over structure (24) onto the interconnecting material (26) includes disposing an over structure (24) onto the interconnecting material (26) having an inner contour which is compatibly configured with respect to the outer contour of the base structure (16) such that the interconnecting material (26), as the over structure (24) is disposed onto the interconnecting material (26), extends into and fills the interspatial area between the base structure (16) and the over structure (24) in a manner by which the interconnecting material (26) assumes a substantially uniform thickness in the interspatial area between the base structure (16) and the over structure (24).

15. A method for producing a dental restoration according to claim 13, wherein the step of disposing the over structure (24) onto the interconnecting material (26) includes disposing the over structure (24) onto the interconnecting material (26) by pressing the over structure (24) onto the not yet completely activated interconnecting material (26).

16. A method for producing a dental restoration according to claim 13, wherein the over structure (24) partially covers the base structure (16) such that a portion of the base structure (16) is uncovered.

* * * * *